(12) United States Patent
Figures

(10) Patent No.: US 11,052,219 B2
(45) Date of Patent: Jul. 6, 2021

(54) SENSORY ACTIVITY SACK

(71) Applicant: Ida Figures, Bakersfield, CA (US)

(72) Inventor: Ida Figures, Bakersfield, CA (US)

( * ) Notice: Subject to any disclaimer, the term of this patent is extended or adjusted under 35 U.S.C. 154(b) by 516 days.

(21) Appl. No.: 15/591,453

(22) Filed: May 10, 2017

(65) Prior Publication Data

US 2018/0326175 A1    Nov. 15, 2018

(51) Int. Cl.
*A61F 5/37* (2006.01)
*A61M 21/02* (2006.01)
*A41D 27/08* (2006.01)
*A41D 27/28* (2006.01)
*A41D 11/00* (2006.01)
*A41D 10/00* (2006.01)
*A41D 13/12* (2006.01)
*A61M 21/00* (2006.01)

(52) U.S. Cl.
CPC ............ *A61M 21/02* (2013.01); *A41D 10/00* (2013.01); *A41D 11/00* (2013.01); *A41D 13/1245* (2013.01); *A41D 27/08* (2013.01); *A41D 27/28* (2013.01); *A61F 5/37* (2013.01); *A61M 2021/0066* (2013.01)

(58) Field of Classification Search
CPC ... A61M 21/02; A47D 15/005; A47D 15/008; A47D 15/006; A61F 5/37; A61F 5/3715; A61F 5/3784; A61F 5/3723; A61F 5/373; A61F 5/3738; A61F 5/3776; A61F 5/3746; A61F 5/3769; A41B 13/06; A41B 13/08; A41B 13/065; A41B 13/00; A41D 11/00; A45F 4/08; A47G 9/08; A47G 9/083; A47G 9/086

USPC .......... 128/873, 874, 875, 846, 878
See application file for complete search history.

(56) References Cited

U.S. PATENT DOCUMENTS

| | | | | | |
|---|---|---|---|---|---|
| 2,651,781 | A | * | 9/1953 | Buchholz | A41B 13/06 2/69.5 |
| 2,828,738 | A | * | 4/1958 | Strelakos | A61F 5/3723 128/874 |
| 3,924,273 | A | * | 12/1975 | Donovan | A41D 10/00 2/69.5 |
| 4,688,270 | A | * | 8/1987 | Denicola | A41D 13/1272 128/874 |
| 8,607,364 | B2 | * | 12/2013 | Barski | A41B 13/06 2/111 |
| 2009/0064390 | A1 | * | 3/2009 | Beiring | A41B 13/06 2/80 |
| 2012/0125347 | A1 | * | 5/2012 | Soileau | A41B 13/06 128/873 |

(Continued)

*Primary Examiner* — Victoria J Hicks
(74) *Attorney, Agent, or Firm* — Matthew C. McCartney

(57) ABSTRACT

A sensory activity sack provides a garment with pleasant tactile features offering safe sensory stimulation for persons with developmental or sensory disabilities and an isolation bag for the wearer's arms and hands. The isolation bag prevents the wearer from engaging in self-injurious behavior or other harmful behaviors. Multiple fabrics and textures in the isolation bag, including mesh and denim, provide a pleasing tactile experience, which can be furthered by the placement of toys into the isolation bag. Sensory panels made with a sturdy, textured material such as denim provide tactile stimulation and resistance against wear and biting, as well as adding a comforting weight to the sensory activity sack for wearers with sensory issues.

18 Claims, 7 Drawing Sheets

(56) References Cited

U.S. PATENT DOCUMENTS

| | | | | |
|---|---|---|---|---|
| 2012/0311762 A1* | 12/2012 | Aiken | ................... | A41B 13/06 |
| | | | | 2/69.5 |
| 2017/0006924 A1* | 1/2017 | Patterson | ............... | A41B 13/06 |
| 2017/0318984 A1* | 11/2017 | Parker | ................... | A41B 13/06 |

* cited by examiner

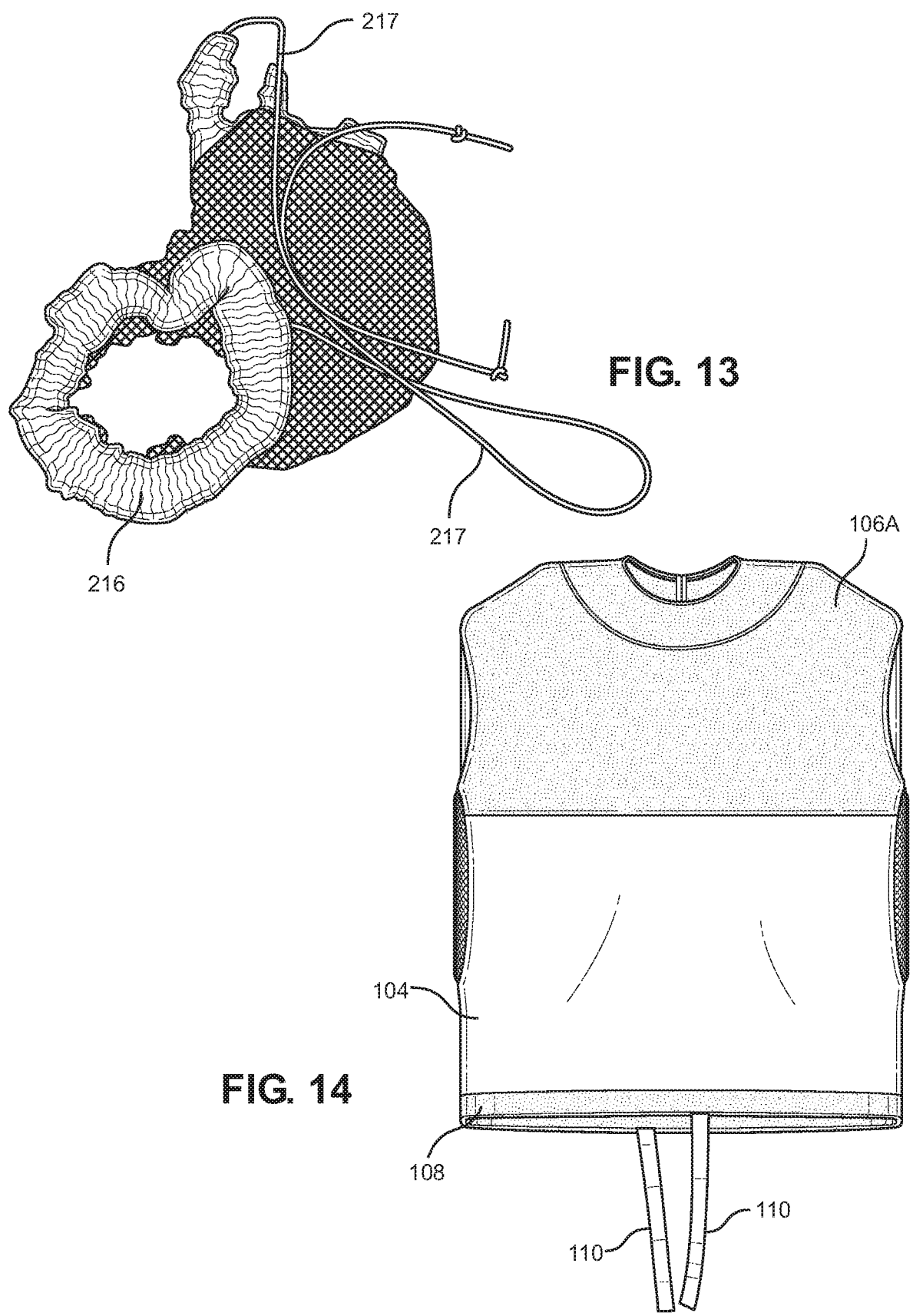

SENSORY ACTIVITY SACK

FIELD OF THE INVENTION

The present invention pertains generally to a sensory garment for persons diagnosed with a disorder affecting sensory processing. More specifically, the present invention pertains to a garment that prevents a person from harmful activities while providing safe sensory stimulation. The present invention is particularly, but not exclusively, useful as a garment for children diagnosed with autism, sensory processing disorder, or other developmental or behavioral disorders.

BACKGROUND OF THE INVENTION

Self-injurious behavior ("SIB") accompanies a variety of disorders, including several personality disorders, mental disorders, and developmental disorders. Persons with certain neurological or developmental disabilities, including Rett syndrome, Angelman syndrome, and those in the autism spectrum often manifest self-injurious behaviors, as well as other harmful or socially inappropriate behaviors not falling under the umbrella of SIB.

SIB in persons with developmental disabilities may include scratching or biting oneself, head-banging, punching or hitting oneself in the head or other areas of the body, excessive rubbing, as well as many other behaviors. These behaviors may occur in response to frustration, pain, or other factors, and may be caused or exacerbated by seizures or other physiological factors.

Pica is another undesirable and potentially harmful behavior that sometimes accompanies developmental disabilities. Pica involves the tendency to consume non-food items. For example, in the case of a person with developmental disabilities who by necessity must wear a diaper, this may include picking at and eating the diaper or its contents. Such behavior may be a manifestation of an already diagnosed disorder, or may be diagnosed on its own as "pica."

Attempts are often made to control harmful behaviors in persons with developmental disabilities through medication or negative and positive reinforcement. In serious cases, therapy involving electric shocks as negative reinforcement for inappropriate behavior has been used, and such therapy has generated controversy. Weighted blankets or compression clothing has been used with positive results in some cases. Nevertheless, attempts to treat the behavior are not always successful, and often it is necessary to restrain the person engaging in the harmful behavior.

In light of the above, it would be advantageous to provide an apparatus, such as a garment, for restraining a person from engaging in harmful behaviors while allowing the restrained person sufficient freedom to interact with others. It would be further advantageous to provide a restraining apparatus which provides sufficient sensory stimulation so that the restrained person is not overly frustrated by the restraints.

It would be further advantageous to provide a garment that has easy access to undergarments to facilitate the changing of a diaper without removal of the garment.

It would be further advantageous to provide a restraining garment that has ornamental appearance and disguises the restraints.

Finally, it would be further advantageous to provide a restraining garment that allows the wearer use of his or her hands and freedom of movement within the garment to enable the wearer to interact with his or her surroundings safely.

SUMMARY OF THE INVENTION

The present invention is directed to a sensory activity sack that gently restrains a person with a developmental disability or other disorder that includes harmful behaviors. The restraint provided by the sensory activity sack is limited to prevent the undesirable behaviors while allowing the person the freedom to move, stretch, and interact with others. Furthermore, the sensory activity sack provides sensory stimulation to the person wearing it.

The sensory activity sack has an inner isolation bag within an outer garment. The outer garment has an outer front panel and an outer rear panel hemmed together to form an open neck and an open bottom. The outer garment does not have sleeves found in typical garments. Instead, the sides of the outer garments are equipped with ventilation openings to allow air to enter the interior of the outer garment. The outer rear panel is equipped with a zipper to facilitate quick dressing and undressing.

The top and bottom of the outer garment each is formed with a weighted sensory fabric selected so as to provide comfort to a wearer with sensory issues. More specifically, the top of the outer garment has a top sensory panel that encircles the open neck and extends over the shoulders and across the upper back and upper chest. In an embodiment, the top sensory panel is made from a weighted sensory fabric, such as thick denim. Similarly, the bottom of the outer garment has a bottom sensory panel made from the bottom of the outer front and outer rear panels that increases the weight of the garment. The bottom of the outer garment is also formed with tie ends that can be tied to one another in order to close the open bottom.

Between the top sensory panel and the bottom sensory panel is a decorative thinner material that may optionally be equipped with various visually pleasing patterns and colors.

The inner isolation bag has an inner front panel and an inner rear panel formed to create a fully enclosed interior space. Arm through holes are provided on the inner rear panel of the inner isolation bag and are sized to receive the hands and arms of a wearer such that the hands and arms are located within the fully enclosed space. These arm through holes provide the only access to the fully enclosed space of the inner isolation bag. The top of the inner isolation bag is connected to the interior of the outer front panel of the outer garment at a connection seam. Once so connected, the inner isolation bag is contained entirely within the outer garment.

The inner isolation bag is made from a lightweight fabric at the top and sides coupled with a heavyweight fabric on the bottom to provide alternative sensory inputs for the wearer. Both the lightweight fabrics and the heavyweight fabrics should be selected from fabrics that reduce discomfort and provide pleasant sensory stimulation to the wearer.

In use, the open bottom of the outer garment is placed over the head of the wearer of the garment by a caregiver. With the zipper unzipped, the caregiver then has adequate access to gently direct each hand into and through the respective arm through holes until both hands and arms are inside the inner isolation bag and the shoulders of the wearer are located at the left and right arm through holes. Before placing the wearer's arms into the arm through holes, comforting objects, such as toys, or other therapeutic devices can be placed through the arm through holes and into the fully enclosed interior space. Alternatively, the inner isolation bag may have an access opening that can be easily opened and closed, with a secure fastener such as a zipper.

Once the arms of the wearer are passed through the arm through holes, the zipper is zipped up to secure the outer garment around the neck and shoulders of the wearer. Next, the ties are tied together between the legs of the wearer to close the bottom of the outer garment.

In use, the wearer has sufficient space within the fully enclosed interior space to interact with any objects placed in the fully enclosed interior space. Further, the inner isolation bag and outer garment are each sized to enable the wearer to touch his or her face through the fabric as well as other portions of his or her body. The wearer of the outer garment can have his or her arms retrained simply by wearing the outer garment. However, certain wearers benefit from additional restraint, such as those with pica. The inner isolation bag prevents access to the diaper as well as objects located outside of the inner isolation bag. The inner isolation bag provides sufficient restraint to protect the wearer from engaging in harmful conduct, such as pica, but otherwise provides enough freedom of movement to allow the wearer to feel comforted.

BRIEF DESCRIPTION OF THE DRAWINGS

The nature, object, and advantages of the present invention will become more apparent to those skilled in the art after considering the following detailed description in connection with the accompanying drawings, in which like reference numerals designate like parts throughout, and wherein:

FIG. 13 is a front view of the arm hole binding strip of FIG. 12 in its tightened or closed configuration with the drawstring pulled out and tied; and FIG. 14 is a front view of the sensory activity sack showing an embodiment of the top sensory panel in which the top sensory panel extends across the front of the garment and down a substantial portion of the front of the garment.

DETAILED DESCRIPTION OF A PREFERRED EMBODIMENT

The present invention provides sensory activity sack capable of providing a pleasant tactile experience to a wearer while protecting from harmful behaviors.

Figure 1:
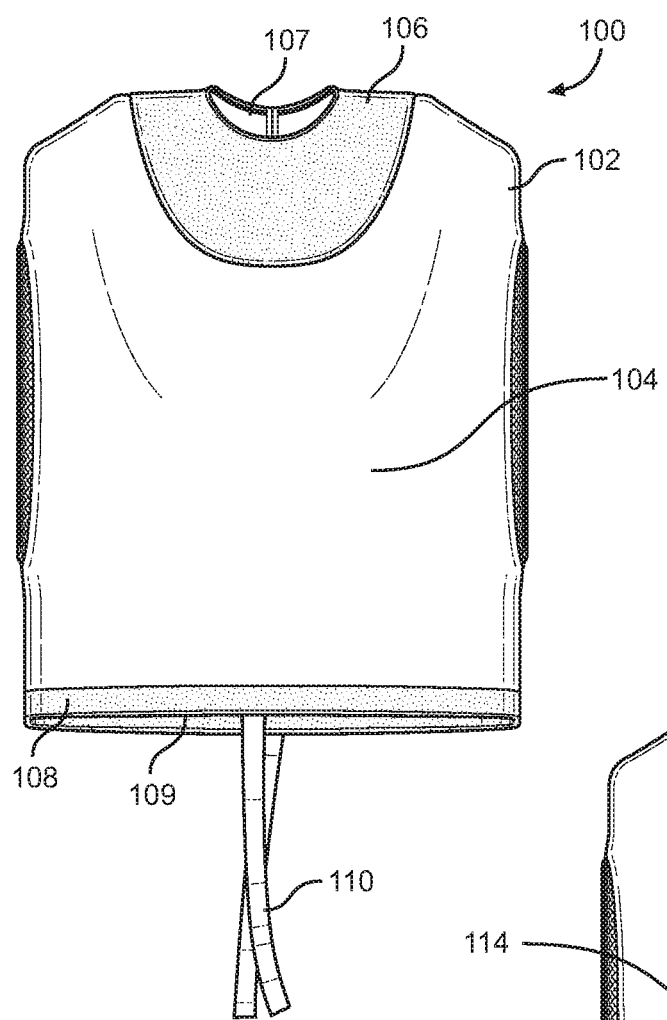
FIG. 1 is a front view of the sensory activity sack of a preferred embodiment of the present invention showing the outer garment with an upper sensory panel encircling the neck opening and covering the upper chest area of the outer garment, a decorative layer, and a lower sensory panel.

Referring initially to FIG. 1, a sensory activity sack is shown in a front view and generally designated 100. Sensory activity sack 100 comprises an outer garment 102 with an outer front panel 104, which may be made of decorative or otherwise comfortable material. A top sensory panel 106 made up of a weighted sensory fabric sits around a neck opening 107 centered in the upper end of the outer garment 102. The inventor has found that wearers find denim more pleasing than other fabrics for use as a weighted sensory fabric for sensory panels in the sensory activity sack 100. Moreover, since the wearer may have a tendency to chew on the upper part of his or her clothing, a top sensory panel 106 made of a sturdy, textured fabric such as denim will resist tearing in addition to providing needed sensory stimulation to the wearer. The top sensory panel 106 also adds weight to the garment, providing comfort to wearers with certain sensory issues. A bottom sensory panel 108, placed around a bottom opening 109, is also made of a weighted sensory fabric such as denim, and provides additional weight to the garment to help with sensory issues.

Figure 2:
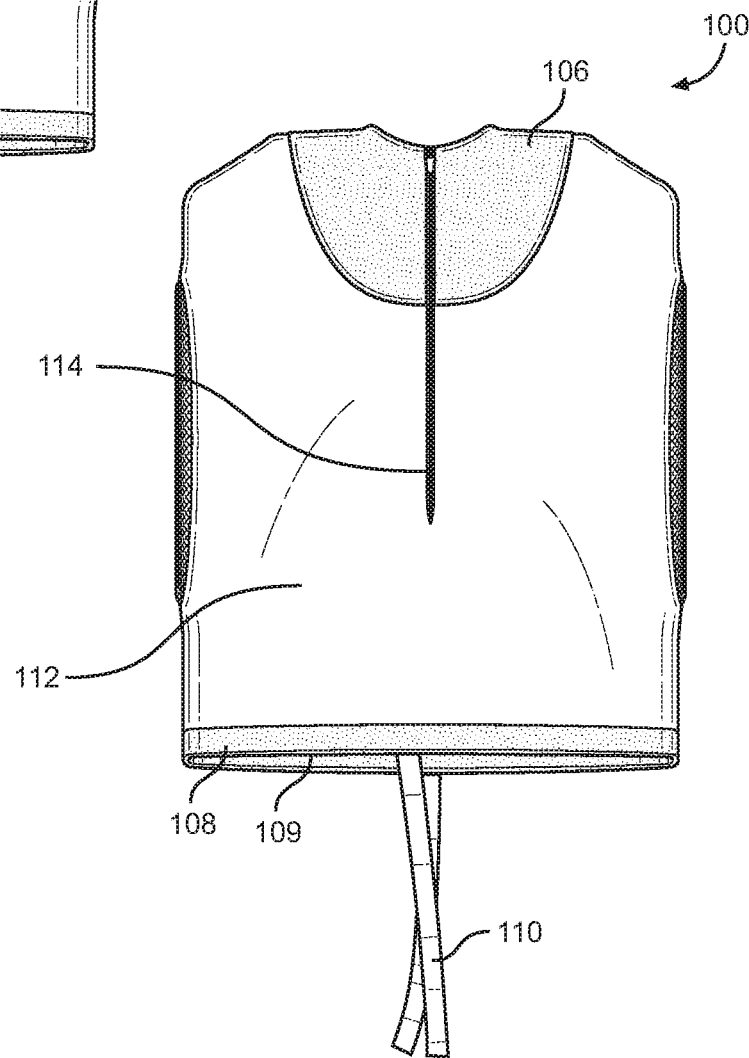
FIG. 2 is a rear view of the sensory activity sack of a preferred embodiment of the present invention showing the outer garment with a zipper and slider to enable easy dress and undress of the sensory activity sack.

Referring now to FIG. 2, an outer rear panel 112 of the sensory activity sack 100 includes a zipper 114 to secure the sensory activity sack 100 on the wearer. A clip (not shown) on the inside of the garment at the top of the zipper 114 further secures the sensory activity sack 100 on the wearer.

Figure 3:
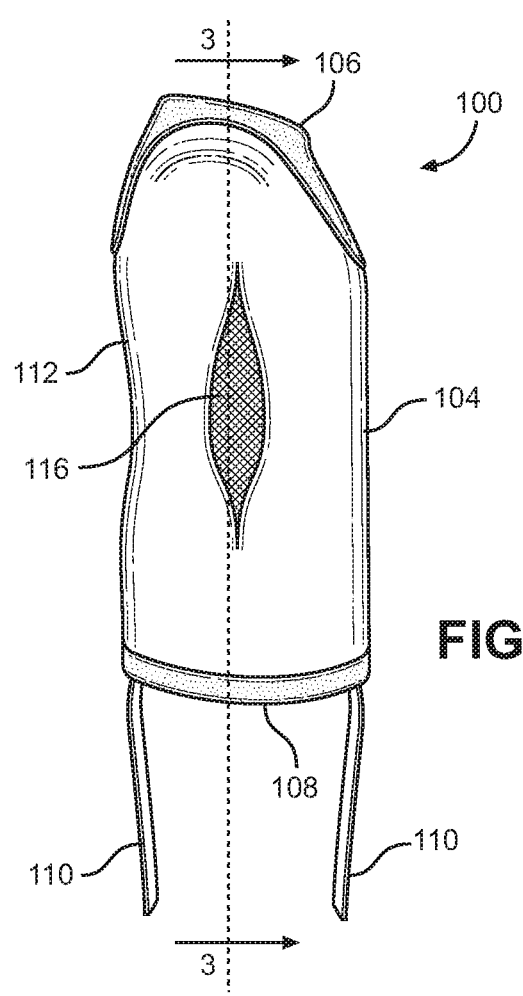
FIG. 3 is a right side view of the sensory activity sack showing the outer garment with a ventilation opening designed to provide cooling ventilation to a wearer of the sensory activity sack and lower attachment straps for easy access to undergarments such as patents and/or a diaper.

Referring now to FIG. 3, a side view of the sensory activity sack 100 is shown. A ventilation opening 116 on each side of the sensory activity sack allows air to enter the interior of the outer garment. A mesh or netted material is sewn onto the interior of the sensory activity sack 100 on each side and covers the ventilation openings 116. The front and the back of the sensory activity sack each have a separate tie 110 comprising a rectangular piece of fabric with one end sewn into opposing ends of the inner side of the bottom sensory panel 108. The ties 110 act as an attachment strap which allows the garment to be tied or otherwise secured between the legs of the wearer in order to provide stability and prevent removal of the garment by the wearer. The bottom sensory panel 108 provides a useful attachment point for the ties 110. Variations on the attachment strap may include snaps, buttons, or other connectors which allow the garment to be secured by snapping or other means rather than tying.

Figure 4:
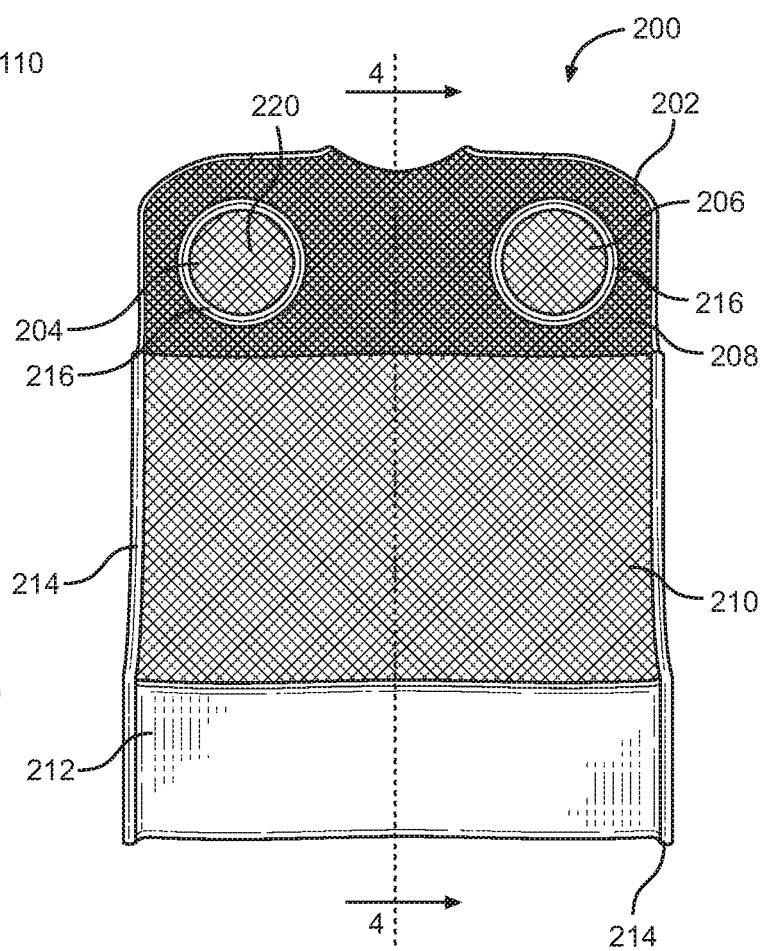
FIG. 4 is a rear view of the inner isolation bag showing through holes for passage of arms into the inner isolation bag and showing different textures of fabrics to address sensory needs.

FIG. 4 shows a rear view of an inner isolation bag 200 of the sensory activity sack 100. The inner isolation bag 200 is formed with an inner front panel 220 and an inner rear panel 202. The inner rear panel 202 has a left arm through hole 204 and a right arm through hole 206 which are sized to receive left and right hands and arms respectively of a wearer such the hands and arms are secured within the inner isolation bag 200. The isolation bag 200 is made of more than one type of fabric, and preferably at least three (3) types of fabric, in order to provide a pleasant tactile experience to the wearer. Toys (not shown in FIG. 4) may be placed in the isolation bag 200, within reach of the wearer. The isolation bag 200 serves to prevent the wearer from accessing the diaper area or engaging in self-injurious behavior while still providing sufficient freedom of movement within the isolation bag 200 to provide comfort to the wearer.

The inner rear panel 202 includes a mesh layer 208 made of a mesh or netted fabric. A lightweight fabric panel 210 on the inner rear panel 202 provides additional weight to the sensory activity sack 100, which has been found to be pleasant to wearers with sensory disorders. The lightweight fabric panel 210 serves the additional useful functions of varying the texture of the inner isolation bag 200 for the wearer and preventing breach of the mesh or netted fabric making up the inner rear panel 202.

A heavyweight fabric bottom 212 of the inner isolation bag 200 provides a third texture for sensory input to the wearer, as well as additional weight to the sensory activity sack 100. Denim provides a good tactile experience when used as the material for the heavyweight fabric bottom 212. The sides of the inner isolation bag 200 are joined by bag binding strips 214, which join together the heavyweight fabric bottom, the inner rear panel 202 to which the lightweight fabric panel 210 is attached in the interior of the inner isolation bag 200, and the inner front panel 220. Above the bag binding strips 214, the upper perimeter of the inner front panel 220 and the inner rear panel 202 are joined together and to the inside of the outer front panel 104 of the sensory activity sack 100 by connection seam 218 (shown in FIG. 5). The heavyweight fabric bottom 212 is made up of a folded heavyweight fabric piece, sealing the perimeter of the inner isolation bag 200 and creating a fully enclosed interior space accessible only via the arm through holes 204 and 206. The left arm through hole 204 and the right arm through hole 206 are each reinforced with an arm through hole binding strip 216.

Figure 5:
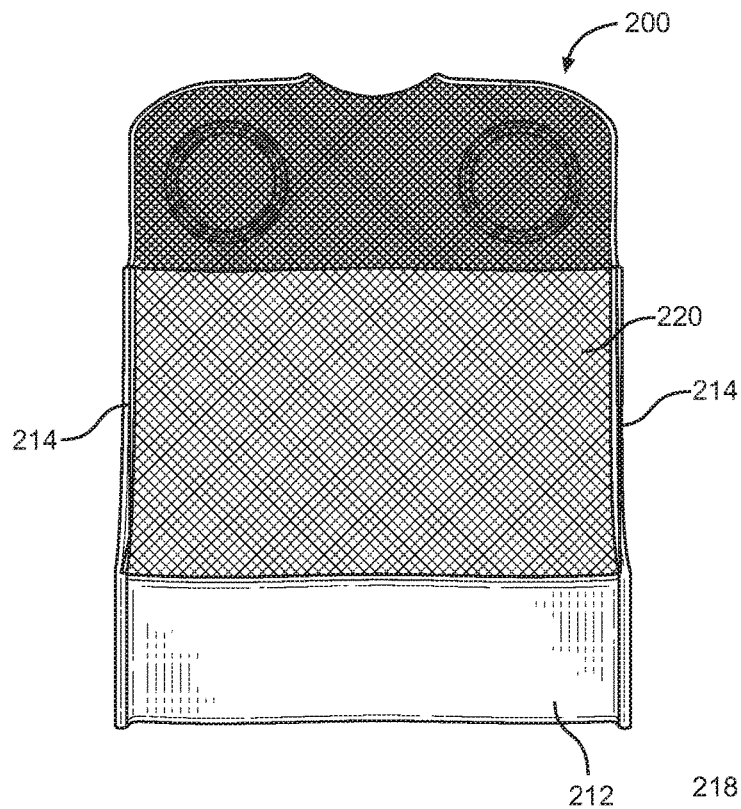
FIG. 5 is a front view of the inner isolation bag showing the mesh layer that makes up the entirety of the inner front panel above the heavyweight fabric bottom.

FIG. 5 is a front view of the inner isolation bag 200, showing the inner front panel 220 made up of a mesh or netted fabric. The inner front panel 220 extends from the top of the inner isolation bag 200 down to the heavyweight fabric bottom 212. The sides of the inner front panel 220 are joined to the inner rear panel 202 by the bag binding strips 214, which extend down to close the sides of the heavyweight fabric bottom 212 also.

Figure 6:
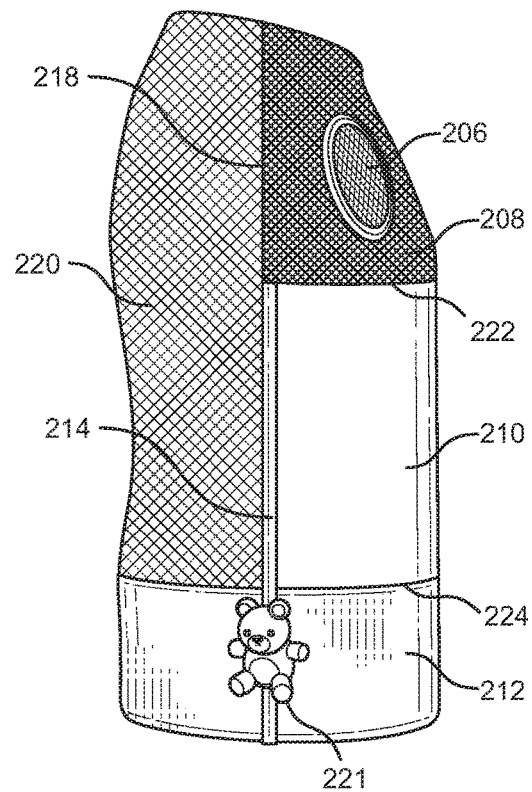
FIG. 6 is a cross-sectional view of the inner isolation bag taken along the lines 4-4 shown in FIG. 4 and showing the separate fabrics of the inner back panel consisting of a mesh layer, a lightweight fabric panel, and a heavyweight fabric bottom, the mesh layer and heavyweight fabric bottom of the inner front panel, and a toy placed inside the enclosed interior.

Referring now to FIG. 6, a cross-sectional representation of the inner isolation bag 200 taken along line 4-4 of FIG. 4 is shown. A toy 221 is shown placed in the inner isolation bag 200, allowing the wearer to interact with a safe object. The front of the inner isolation bag 200 has at least two different fabrics with different textures, namely, the mesh or netted fabric of the inner front panel 220, and the heavyweight fabric, such as denim, in the heavyweight fabric bottom 212. The rear of the inner isolation bag 200 has at least two fabric textures, and is shown with three fabric textures in FIG. 6. Naturally, the invention disclosed herein contemplates the inclusion of more than three textures and the desired amount of fabric textures include in the inner isolation bag 200 may be custom tailored to the needs and preferences of the individual wearer. The inner rear panel 202 is made up of a mesh layer 208 attached to the heavyweight fabric bottom 212. A lightweight fabric panel 210 is attached to the inner rear panel 202 by an upper lightweight fabric panel seam 222 binding the lightweight fabric panel 210 to the mesh layer 208 of the inner rear panel 202. A lower lightweight fabric panel seam 224 binds the bottom of the lightweight fabric panel 210 to both the mesh layer 208 of the inner rear panel 202 and the heavyweight fabric bottom. The sides of the lightweight fabric panel 210 are bound to the inner isolation bag 200 by the bag binding strips 214. The at least three textures present in the inner isolation bag provide a varied sensory experience for the wearer, which is generally comforting to the wearer and may be particularly useful for wearers with a sensory disorder. The lightweight fabric panel 210 serves the additional purpose of preventing the wearer from breaching the mesh layer 208 of the inner rear panel 202.

In alternative embodiments, a denim or other heavyweight fabric panel may stand in for the lightweight fabric panel 210. In such cases, the heavyweight fabric panel would be attached to the inner rear panel 202 of the inner isolation bag 200 in substantially the same manner as described above with respect to the lightweight fabric panel 210.

Figure 7:
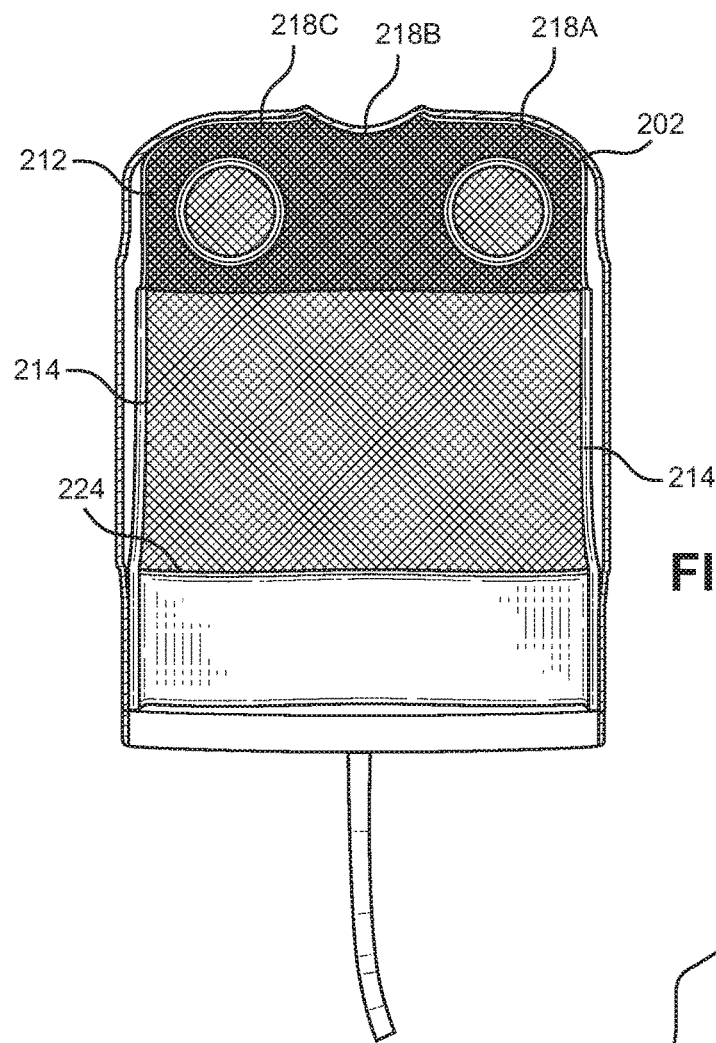
FIG. 7 is a cross sectional view of the sensory activity sack taken along the lines 3-3 shown in FIG. 3 and showing the attachment point of the inner isolation bag to the interior of the outer garment.

Referring now to FIG. 7, a cross-sectional representation of the sensory activity sack 100 taken along line 3-3 from FIG. 3 is shown, and the connection seam 218A, 2188, and 218C attaching the inner isolation bag 200 to the outer garment 102 of the sensory activity sack 100 is shown. A right-side connection seam 218A binds together the inner rear panel 202 and the inner front panel 220 along the upper right of the inner isolation bag 200 and the outer garment 102. The right-side connection seam 218A extends from the right end of the neck opening 107 of the outer garment 102 to the top of the bag binding strip 214 on the right side of the inner isolation bag 200. Thus, the inner isolation bag 200 is attached to the outer garment 102 around the shoulder area, but remains separate from the outer garment 102 below the arm holes. A neck-area connection seam 218B binds the inner isolation bag 200 to the outer front panel 104 around the neck opening 107 of the outer garment 102. A left-side connection seam 218C extends from the left end of the neck opening 107 of the outer garment 102 to the top of the bag binding strip 214 on the left side of the inner isolation bag 200. The connection seams 218A, 218B, and 218C bind the inner front panel 220 and the inner rear panel 202 to each other and to the outer garment 102, up to the points where the bag binding strips 214 bind the inner isolation bag panels together, thus providing a fully enclosed interior space and isolating the wearer's arms.

Preferred embodiments use a four-thread overlock stitch for left-side connection seam 218C and right-side connection seam 218B Around the neck area, a single-needle lockstitch or a cover stitch is used for the neck-area connection seam 2186, in part because the neck-area connection seam 2186 is visible on the outside of the outer garment 102. More particularly, the neck-area connection seam 218B is visible along the upper perimeter of the top sensory panel 106 around the front of the neck opening 107 of the outer garment 102.

As shown, in preferred embodiments the lightweight fabric panel 210 has its top edge at or below the top edges of the bag binding strips 214. Thus, the bag binding strips 214, rather than the connection seams 218A and 218C, connect the sides of the lightweight fabric panel 210 to the inner isolation bag. The top of the lightweight fabric panel 210 is attached to the inner rear panel 202 of the inner isolation bag 200 by a seam 222, and the bottom of the lightweight fabric panel 210 is attached to both the inner rear panel 202 and the top of the rear panel side of the heavyweight fabric bottom 212 by another seam 224.

Figure 8:
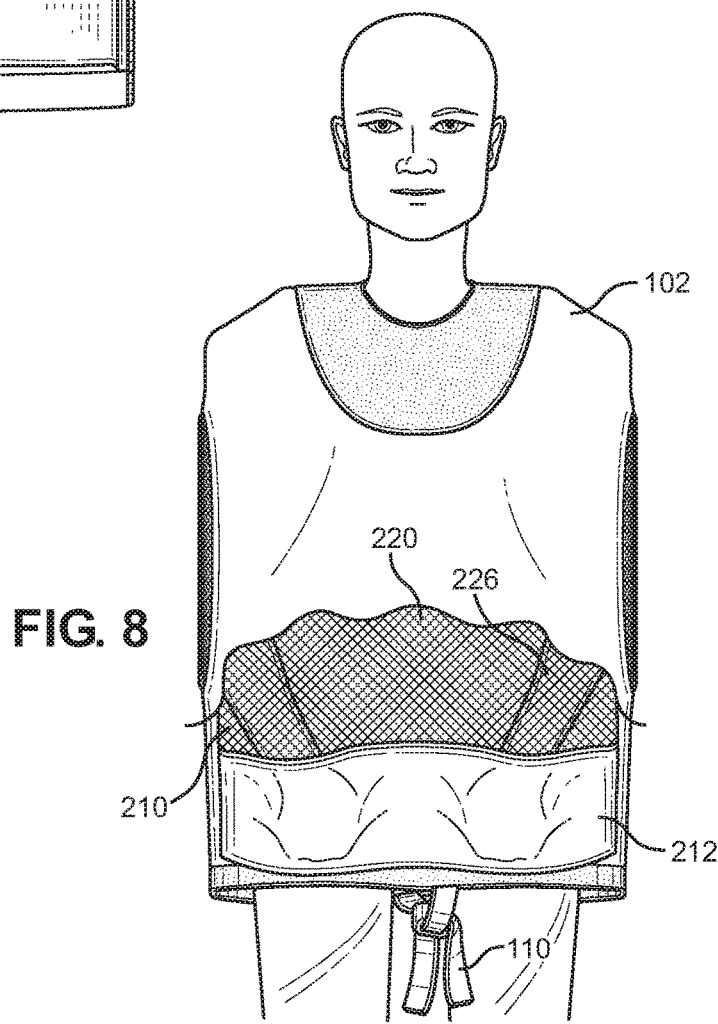
FIG. 8 is a cutaway front view of the sensory activity sack showing the inner isolation bag and further showing arms of a wearer secured within the inner isolation bag.

In FIG. 8, a cutaway view reveals the placement of the wearer's arms 226 into the inner isolation bag 200 while wearing the sensory activity sack 100. As can be seen, the inner front panel 220 of the inner isolation bag 200 is made entirely of a mesh or netted material above the heavyweight fabric bottom 212. The inner rear panel 202, on the other hand, has a lightweight fabric panel 210 above the heavyweight fabric bottom 212, but not extending all the way up to the arm holes 204 and 206. Thus, in preferred embodiments the wearer has at least three different textures in the inner isolation bag 200, which provide for the wearer's sensory stimulation needs. Alternative embodiments may replace the lightweight fabric panel with an additional denim panel. Further stimulation may be provided by toys or other therapeutic items placed in the inner isolation bag 200 within reach of the wearer.

Figure 9:
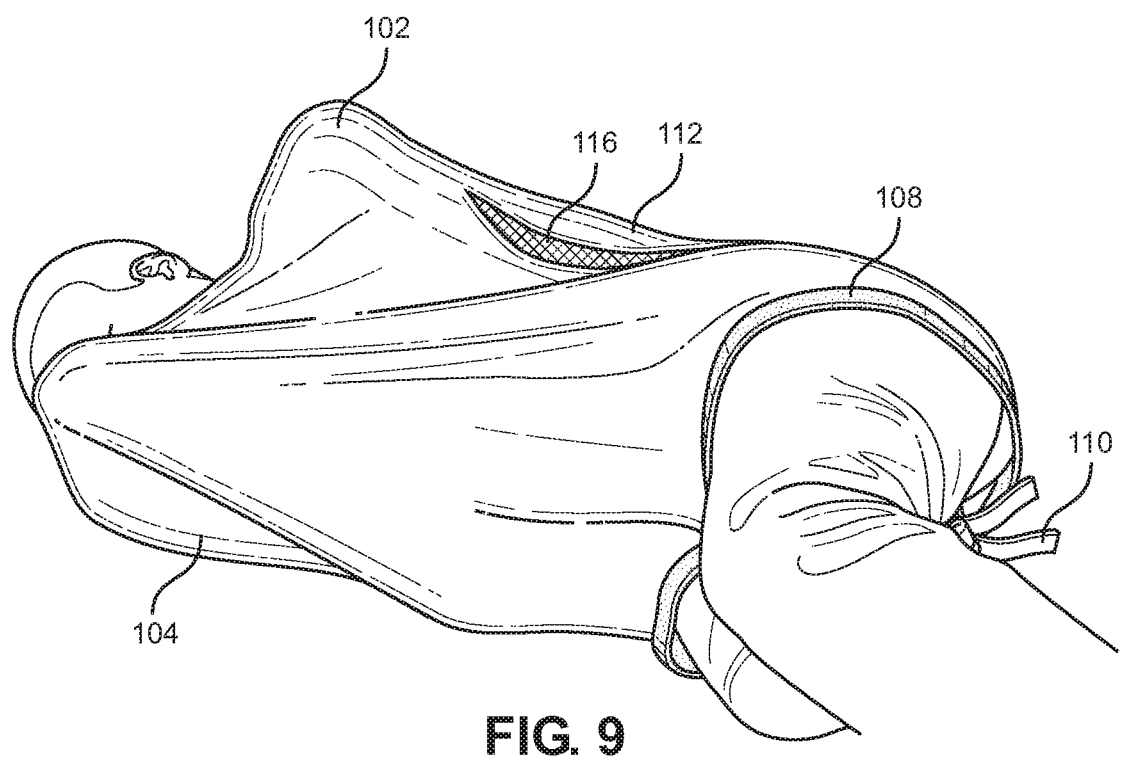
FIG. 9 is a perspective view of the sensory activity sack in use.

Referring now to FIG. 9, the sensory activity sack 100 is shown in use by a wearer. Although the wearer's arms are restrained inside the inner isolation bag 200, the wearer still retains a certain degree of freedom of movement, and is able to access the toys in the inner isolation bag 200 or reach his or her face through the outer garment 102. The ties 110 are tied between the wearer's legs to secure the garment around the wearer.

Figure 10:
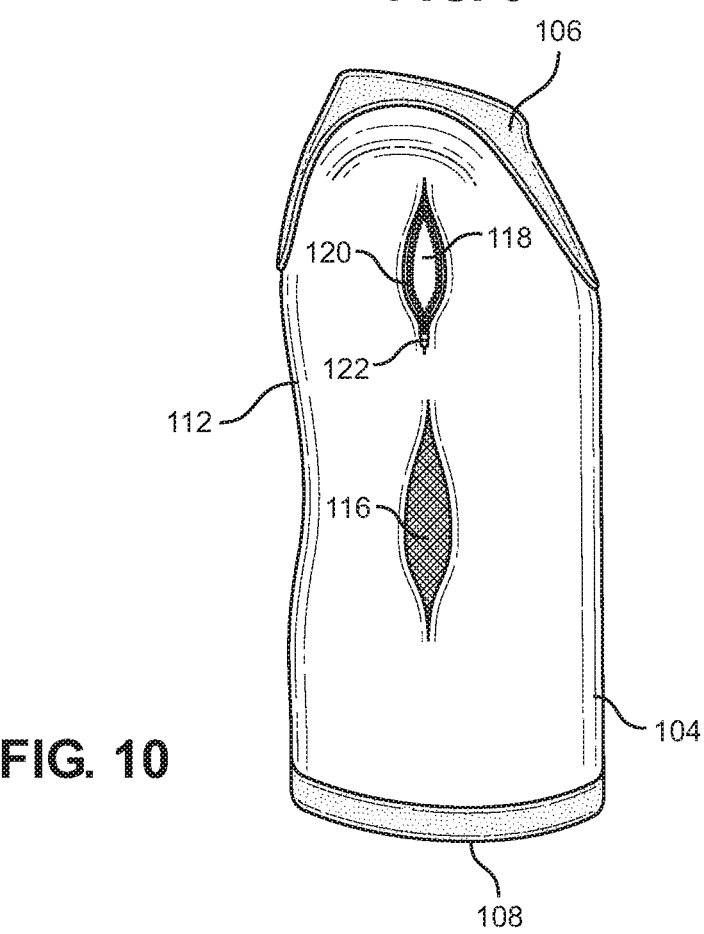
FIG. 10 is a right side view of the sensory activity sack showing an arm opening present in some embodiments.

Referring next to FIG. 10, a right side view of a sensory activity sack 100 is shown comprising an outer front panel 104, a top sensory panel 106, a bottom sensory panel 108, an outer rear panel 112, and ventilation openings 116 on each side (shown only on the visible right side in FIG. 10). An arm opening 118 is present on each side of the outer garment 102 in some embodiments of the sensory activity sack 100. The arm opening 118 allows the wearer's arms to be brought outside the garment for normal use. The wearer's arms can later be placed in the inner isolation bag 200 (shown in FIG. 4) when required to prevent harm to the wearer or others when an episode of aggressive or self-injurious behavior occurs. When not in use, an arm zipper 120 allows for the closure of the arm opening 118 by raising the zipper slider 122. The arm hole 118 can then be opened as needed by lowering the zipper slider 122.

Figure 11:
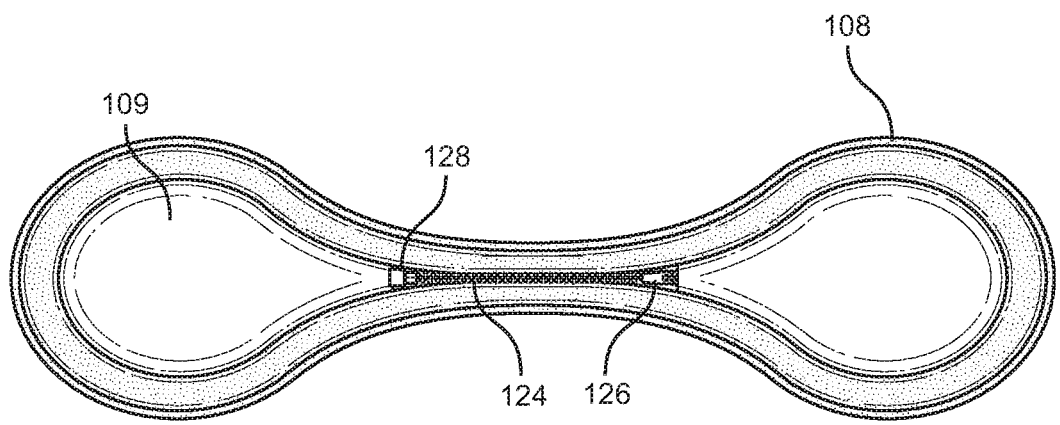
FIG. 11 is a bottom view of the sensory activity sack showing a bottom zipper which may be present in place ties to secure the lower portion of the garment.

Referring now to FIG. 11, a bottom view of a sensory activity sack 100 is shown. As seen in FIG. 11, a bottom zipper 124 may be present in some embodiments of the sensory activity sack 100 in place of the ties 110. If a bottom zipper 124 is present, the lower portion of the sensory activity sack 100 can be secured to the wearer by using the bottom zipper slider 126 to connect the box and pin portion 128 of the bottom zipper 124 and pulling the slider 126 along the zipper 124. To unsecure the bottom portion of the garment in order to remove the sensory activity sack 100, the bottom zipper slider 126 is pulled in the opposite direction to separate the zipper 124 and the box and pin portion 128.

Figure 12:
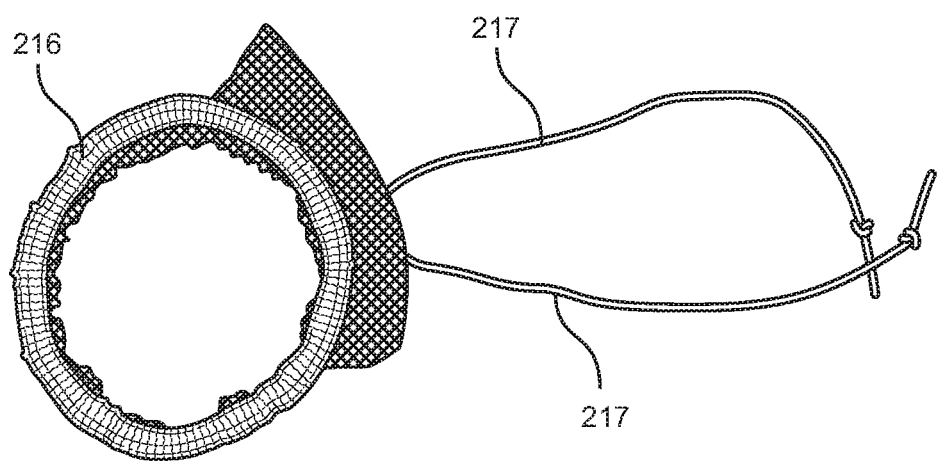
FIG. 12 is a front view of an embodiment of an arm hole binding strip used in the present invention which includes a drawstring to tighten the arm hole.

As shown in FIGS. 12 and 13, some embodiments of the arm hole binding strip 216 may provide a drawstring 217 to better secure the arms of the wearer in the inner isolation bag 200 of the sensory activity sack 100. As seen in FIG. 13, the ends of the drawstring 217 can be pulled out to tighten the arm hole binding strip 216 around the wearer's arms.

Referring now to FIG. 14, a sensory activity sack 100 is shown with an alternate form of top sensory panel, designated 106A. The sensory activity sack may include the larger top sensory panel 106A which extends across the width of the outer front panel 104, and down a substantial portion of the front of the outer garment 102. A larger top sensory panel 106A makes it more difficult for the wearer to pull up on the garment and reach the lighter fabric of the outer front panel 104, thus preventing the wearer from tearing the outer front panel 104 with the wearer's teeth. Since the top sensory panel 106A is made of a heavyweight fabric such as denim, its larger area also provides additional weight, which is comforting to some wearers.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

While there have been shown what are presently considered to be preferred embodiments of the present invention, it will be apparent to those skilled in the art that various changes and modifications can be made herein without departing from the scope and spirit of the invention. Accordingly, the invention is not to be limited as except by the appended claims.

What is claimed is:

1. A sensory activity sack comprising:
   an outer garment formed with an outer front panel and an outer rear panel wherein said outer front panel and said outer rear panel are connected together to form an open neck and an open bottom and wherein said outer garment has an interior surface and an exterior surface;
   an inner isolation bag formed with an inner front panel with an inner front panel perimeter and an inner rear panel with an inner rear panel perimeter wherein said inner front panel and said inner rear panel are connected together at said inner front panel perimeter and said inner rear panel perimeter sealing an inner isolation bag perimeter to form an enclosed space physically separated from the outer garment by said inner front panel and said inner rear panel, where said inner rear panel has a left arm hole to receive a wearer's left hand and arm and a right arm hole to receive a wearer's right hand and arm, said left arm hole and said right arm hole providing a sole access to said enclosed space; and
   wherein said inner isolation bag is connected to said interior surface of said outer garment such that said inner isolation bag is contained entirely within said outer garment and is configured to physically separate and isolate said wearer's left hand and arm inserted through said left arm hole and into said enclosed space and said wearer's right hand and arm inserted through said right arm hole into said enclosed space from an environment between said inner isolation bag and said outer garment.

2. The sensory activity sack of claim 1 further comprising an access opening through said outer garment adjacent said left arm hole and said right arm hole of said inner isolation bag wherein said access opening can be opened and closed with a fastener.

3. The sensory activity sack of claim 1 further comprising one or more ventilation openings in said outer garment.

4. The sensory activity sack of claim 1 further comprising a top sensory panel encircling said open neck of said outer garment.

5. The sensory activity sack of claim 4 wherein said top sensory panel is made from a heavy weight fabric.

6. The sensory activity sack of claim 5 wherein said heavy weight fabric is denim.

7. The sensory activity sack of claim 1 further comprising a bottom sensory panel connected to said inner isolation bag adjacent said open bottom of said outer garment.

8. The sensory activity sack of claim 7 wherein said bottom sensory panel is made from a heavy weight fabric.

9. The sensory activity sack of claim 8 wherein said heavy weight fabric is denim.

10. The sensory activity sack of claim 1 further comprising a front tie connected to said front panel of said outer garment adjacent said open bottom and a rear tie connected to said outer rear panel of said outer garment adjacent said open bottom.

11. The sensory activity sack of claim 1 wherein said inner front panel and said inner rear panel are each made from a mesh material.

12. The sensory activity sack of claim 10 further comprising a bottom sensory panel encircling said open bottom of said outer garment.

13. A sensory activity sack comprising:
an outer garment formed with an outer front panel and an outer rear panel wherein said outer front panel and said outer rear panel are connected together to form an open neck and an open bottom and wherein said outer garment has an interior surface and an exterior surface;
an inner isolation bag consisting of a left arm hole providing sole access to an enclosed space within said inner isolation bag for a left hand and arm of a wearer of said sensory activity sack and a right arm hole providing sole access to said enclosed space within said inner isolation bag for a right hand and arm of said wearer of said sensory activity sack, wherein said inner isolation bag is connected to said interior surface of said outer garment such that said inner isolation bag is contained entirely within said outer garment and said inner isolation bag physically separates said enclosed space from an environment between said inner isolation bag and said outer garment;
an access opening through said outer garment adjacent said left arm hole and said right arm hole of said inner isolation bag wherein said access opening can be closed with a fastener;
a means for closing said open bottom of said outer garment between a left leg and a right leg of said wearer of said sensory activity sack; and
wherein said enclosed space is configured to receive said left hand and arm of said wearer of said sensory activity sack through said left arm hole of said inner isolation bag and configured to receive said right hand and arm of said wearer of said sensory activity sack through said right arm hole of said inner isolation bag to physically separate said left hand and arm and said right hand and arm of said wearer of said sensory activity sack from said environment to prevent said wearer of said sensory activity sack from engaging with said environment and to provide enough freedom of movement to said left hand and arm and said right hand and arm of said wearer of said sensory activity sack in said enclosed space to feel comforted.

14. The sensory activity sack of claim 13 wherein said inner isolation bag is made of a mesh material.

15. The sensory activity sack of claim 14 further comprising a top sensory panel encircling said open neck of said outer garment.

16. The sensory activity sack of claim 15 further comprising a bottom sensory panel connected to said inner isolation bag adjacent said open bottom of said outer garment.

17. The sensory activity sack of claim 16 further comprising one or more ventilation openings in said outer garment.

18. The sensory activity sack of claim 17 further comprising a left arm access and a right arm access in the outer garment, each having an arm zipper allowing said left arm access and said right arm access to be opened and closed by a caregiver.

* * * * *